(12) United States Patent
Bisgaier

(10) Patent No.: US 8,846,761 B2
(45) Date of Patent: Sep. 30, 2014

(54) METHOD FOR TREATING PANCREATITIS

(75) Inventor: Charles L. Bisgaier, Ann Arbor, MI (US)

(73) Assignee: Michigan Life Therapeutics, LLC, Ann Arbor, MI (US)

( * ) Notice: Subject to any disclaimer, the term of this patent is extended or adjusted under 35 U.S.C. 154(b) by 60 days.

(21) Appl. No.: 13/334,384

(22) Filed: Dec. 22, 2011

(65) Prior Publication Data

US 2012/0165411 A1 Jun. 28, 2012

Related U.S. Application Data

(60) Provisional application No. 61/427,236, filed on Dec. 27, 2010.

(51) Int. Cl.
*A61K 31/194* (2006.01)
*A61P 1/18* (2006.01)
*A61K 31/19* (2006.01)

(52) U.S. Cl.
CPC ..................................... *A61K 31/19* (2013.01)
USPC .......................................... 514/574; 562/590

(58) Field of Classification Search
CPC .................................................. A61K 31/194
USPC .......................................... 514/574; 562/590
See application file for complete search history.

(56) References Cited

U.S. PATENT DOCUMENTS

| | | | |
|---|---|---|---|
| 2003/0018013 A1 | 1/2003 | Dasseux et al. | |
| 2003/0149094 A1 * | 8/2003 | Dasseux | 514/449 |
| 2004/0229954 A1 * | 11/2004 | MacDougall et al. | 514/574 |
| 2009/0118317 A1 * | 5/2009 | Bisgaier et al. | 514/277 |

FOREIGN PATENT DOCUMENTS

EP 0369035 A1 5/1990

OTHER PUBLICATIONS

Stella et al. Prodrugs: Challenges and Rewards, Springer New York 2007.*
Fisher et al. Pancreas. In Schwartz's Principles of Surgery, Brunicardi et al., Ed., 9th Edition, McGraw-Hill, New York, 2010, pp. 1167-1243.*
American Heart Association, Third Report of the National Cholesterol Education Program Expert Panel on Detection, Evaluation, and Treatment of High Blood Cholesterol in Adults, Circulation 2002, 106 (25), 3143-3423.*
Mueller et al. J. Med. Chem. 2004, 47, 5183-5197.*
Bays, H.E. et al., "Effectiveness and Tolerability of a New Lipid-altering Agent, Gemcabene, in Patients with Low Levels of High-denisty Lipoprotein Cholesterol", The American Journal of Cardiology, 2003, pp. 538-543, vol. 92.
International Search Report for PCT/US2011/066736, Dated Apr. 17, 2012.
Written Opinion for PCT/US2011/066736, Dated Apr. 17, 2012.

* cited by examiner

Primary Examiner — Sreeni Padmanabhan
Assistant Examiner — Irina Neagu
(74) Attorney, Agent, or Firm — Honigman Miller Schwartz and Cohn LLP; Cynthia M. Bott; Jonathan P. O'Brien

(57) ABSTRACT

Gemcabene, a carboxyalkylether, is effective in the treatment and prevention of pancreatitis in subjects. The compound can be administered in an effective dose as the free acid, a pharmaceutically acceptable salt, or an ester or pro-drug that is hydrolyzed or otherwise metabolized in situ to gemcabene as the free acid or salt thereof.

16 Claims, 8 Drawing Sheets

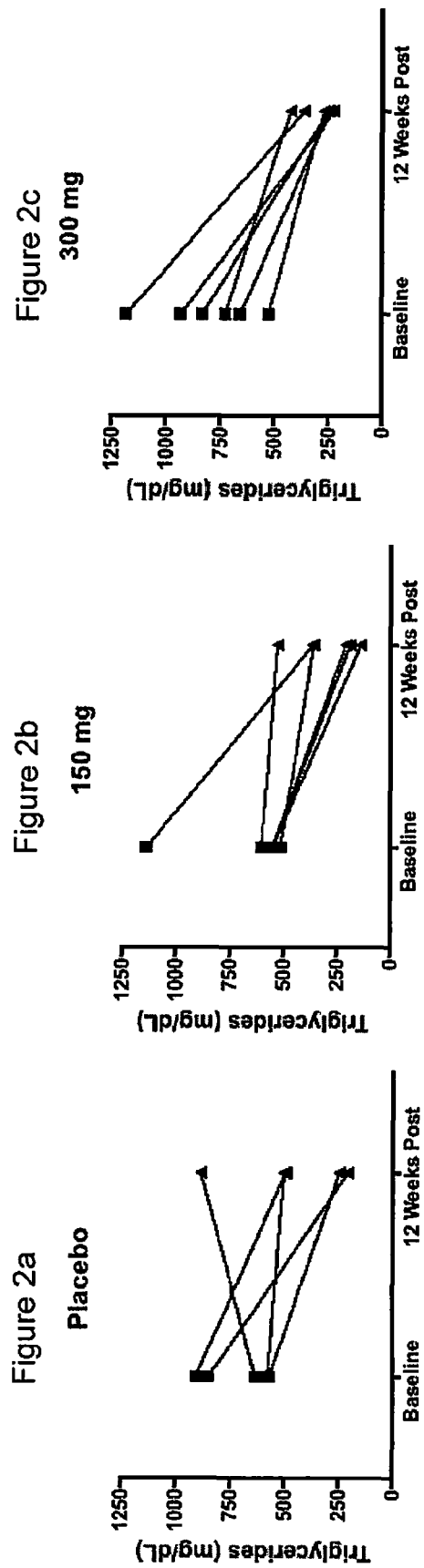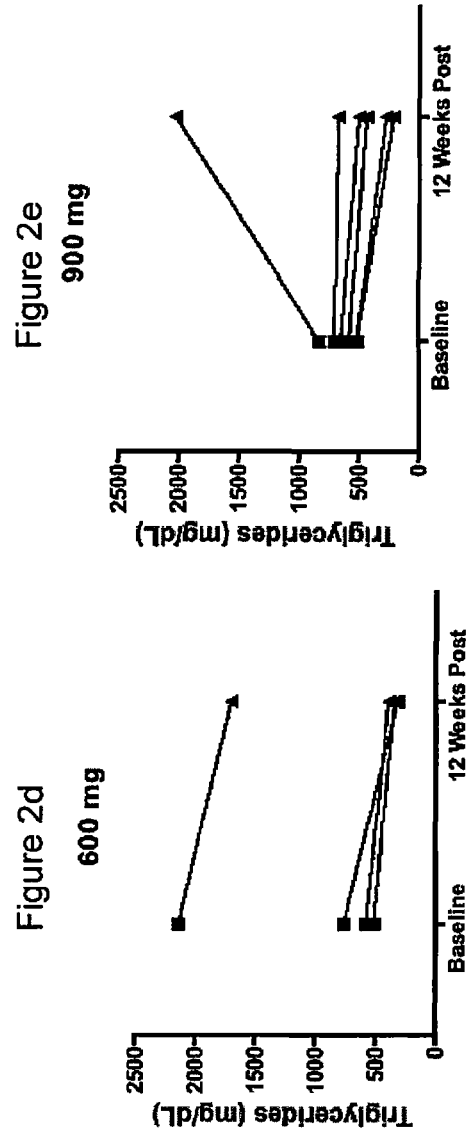

Figure 1:
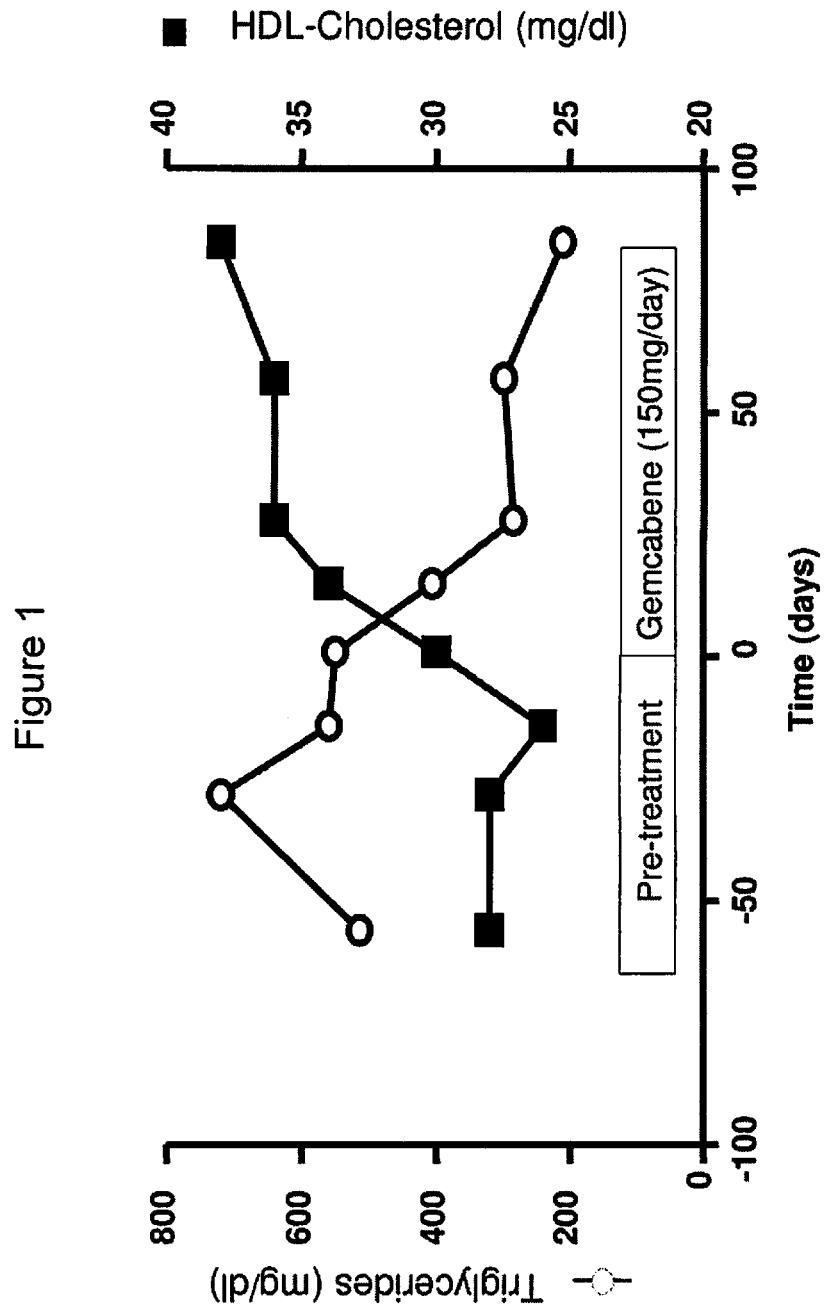
Figure 4C:
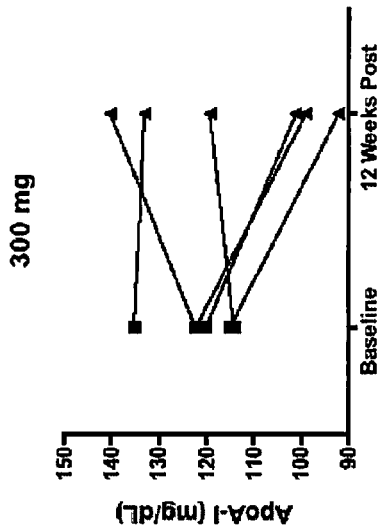
Figure 4B:
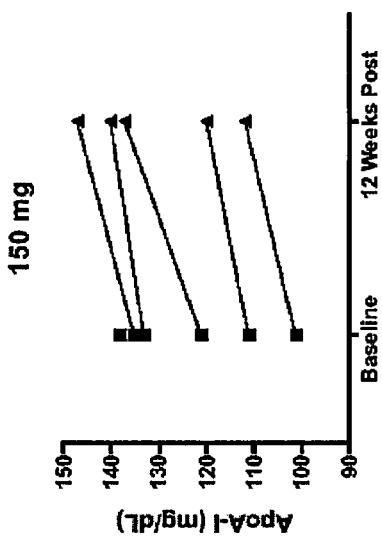
Figure 4A:
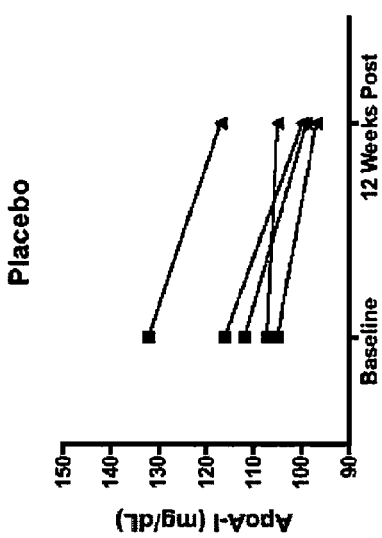
Figure 4E:
Figure 4D:
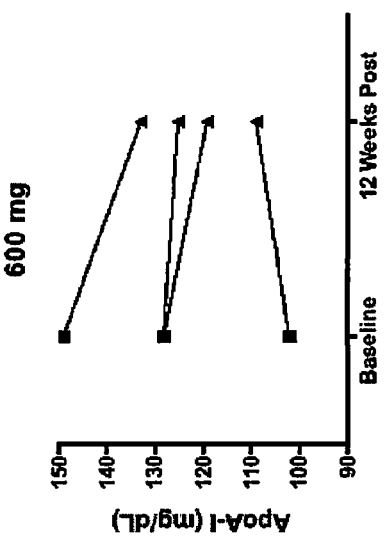

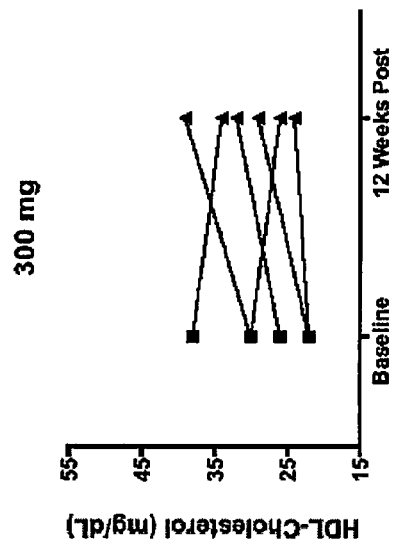
Figure 3a Placebo
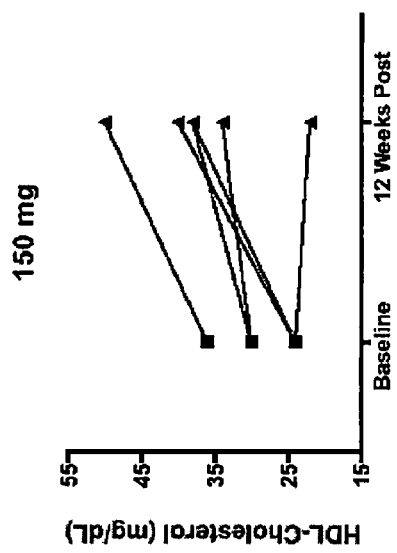
Figure 3b 150 mg
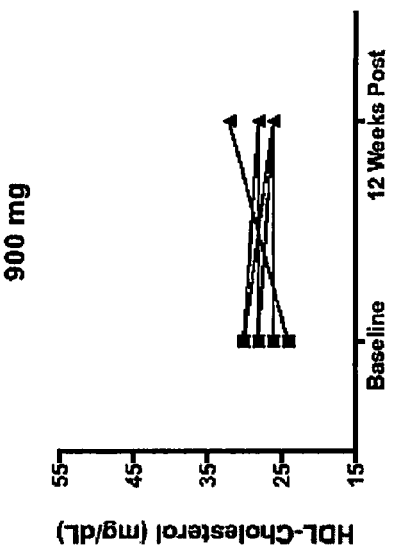
Figure 3c 300 mg
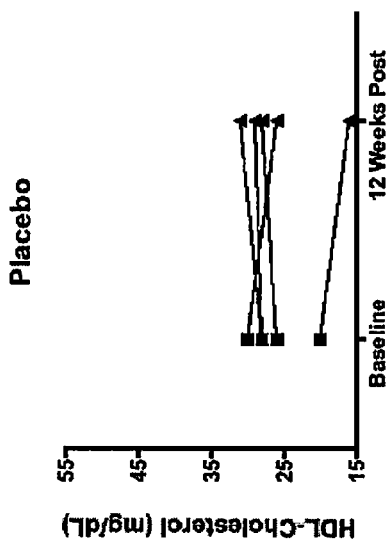
Figure 3d 600 mg
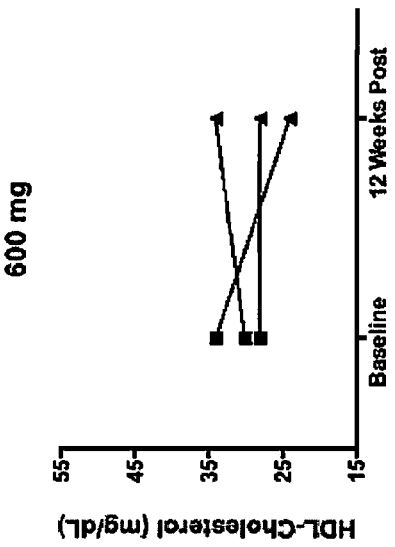
Figure 3e 900 mg 300 mg 150 mg Placebo 900 mg 600 mg

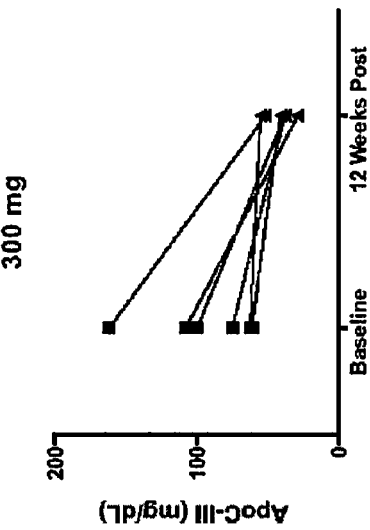
Figure 5a Placebo
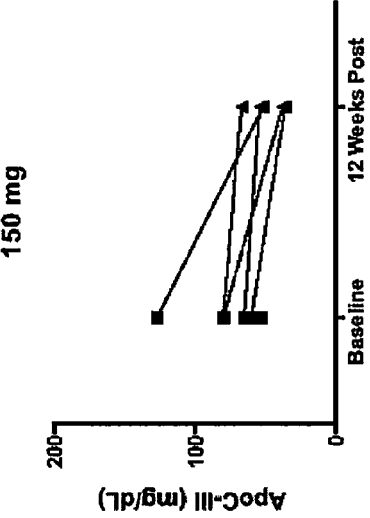
Figure 5b 150 mg
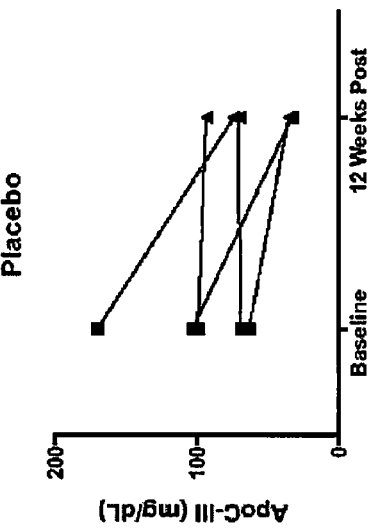
Figure 5c 300 mg
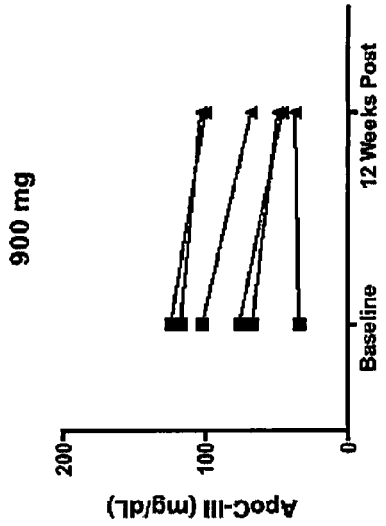
Figure 5d 600 mg
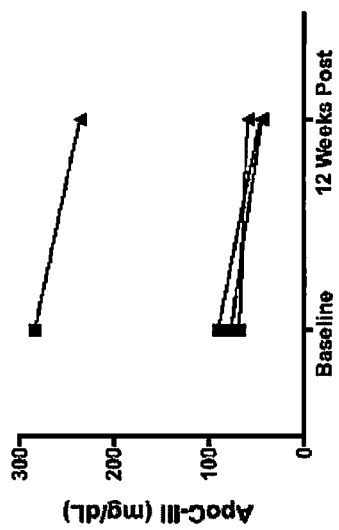
Figure 5e 900 mg

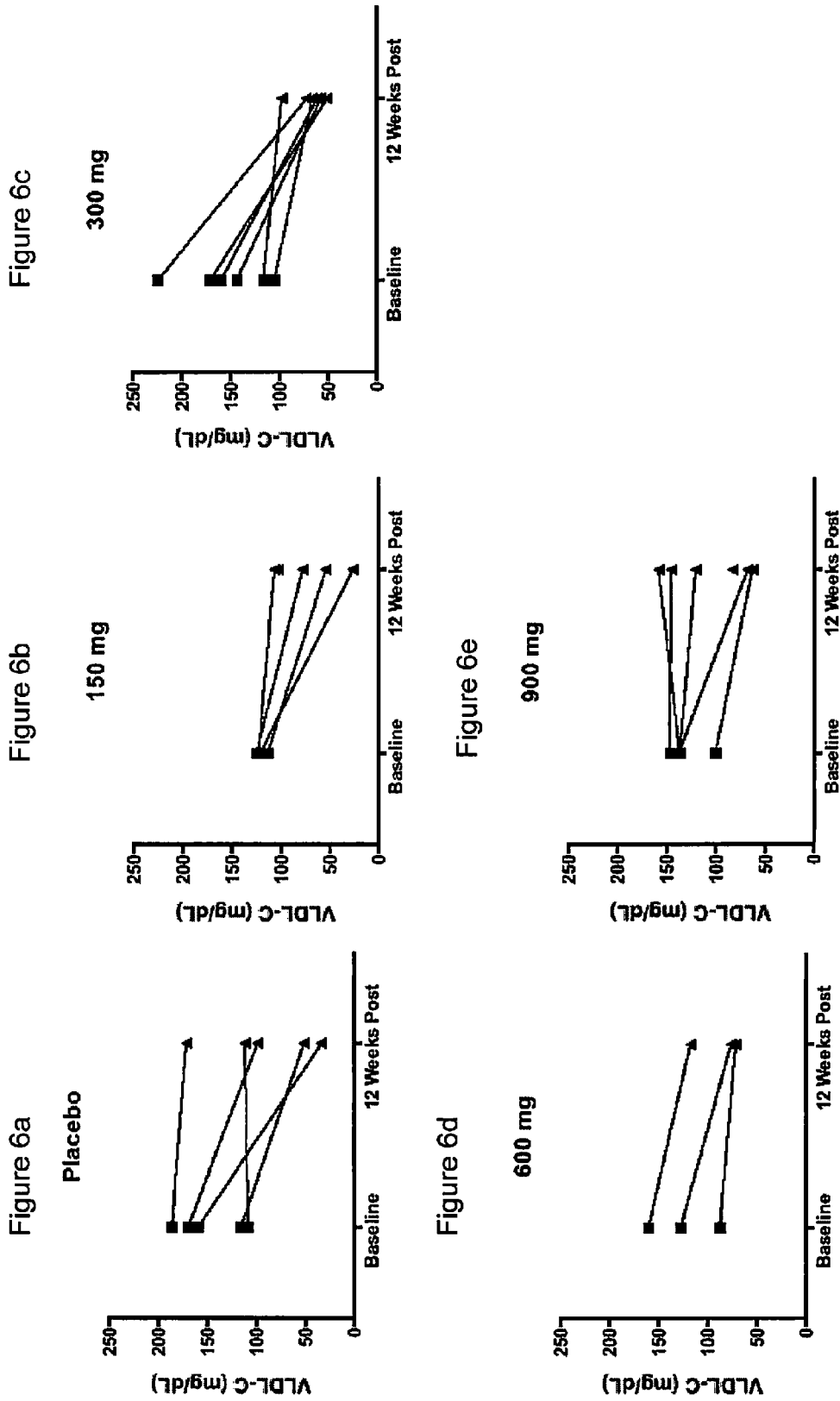

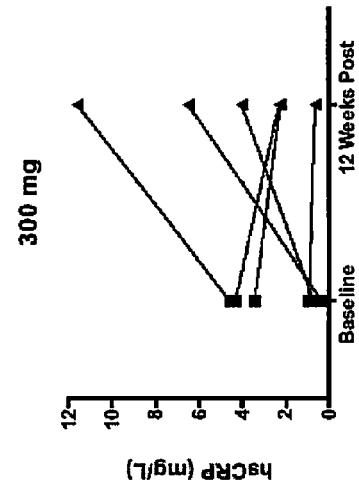
Figure 7a Placebo
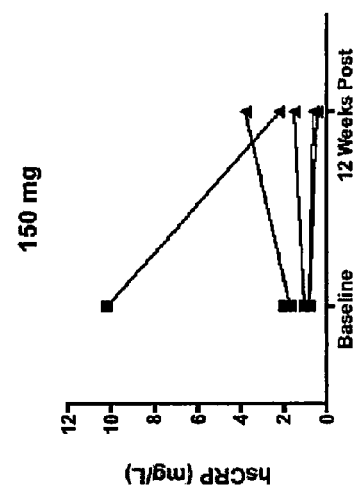
Figure 7d 600 mg
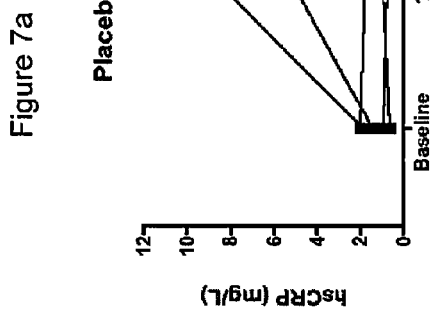
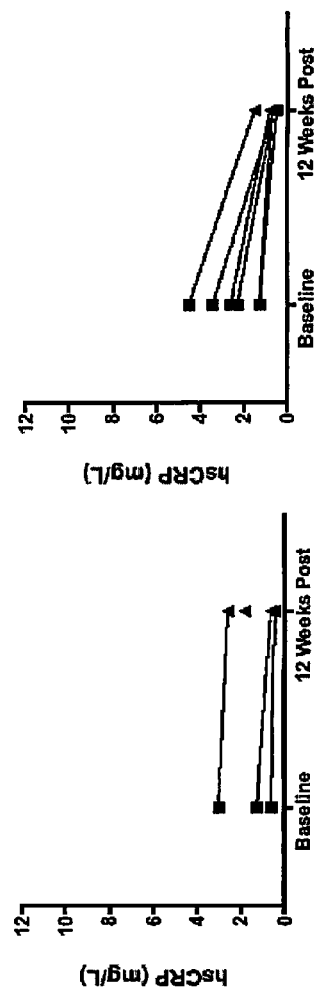

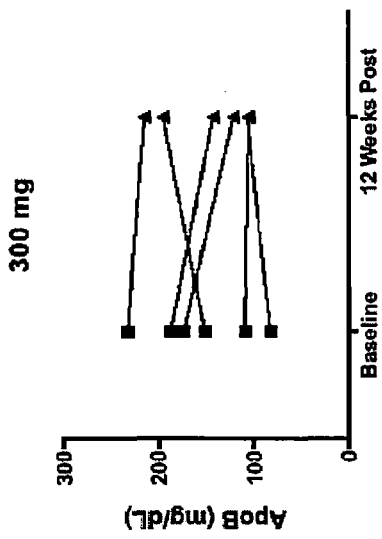
Figure 8a  Figure 8b  Figure 8c
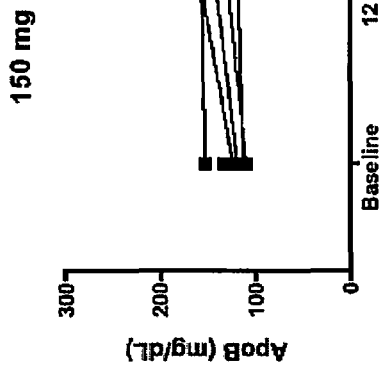
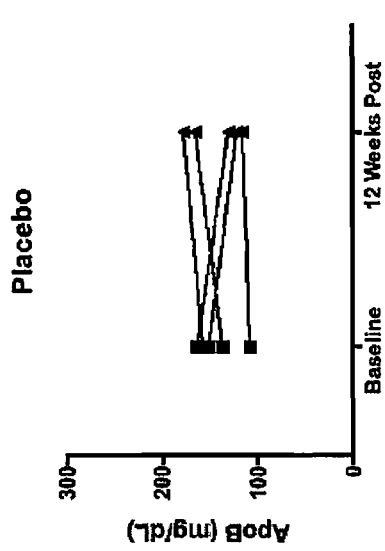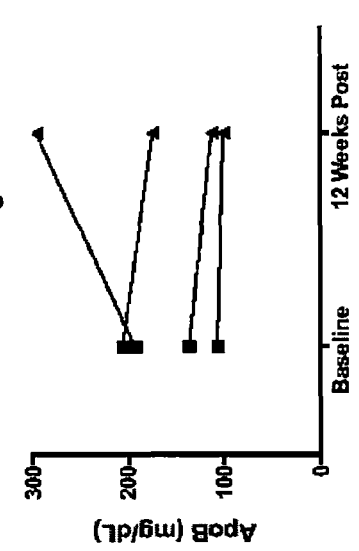
Figure 8d  Figure 8e

METHOD FOR TREATING PANCREATITIS

CROSS REFERENCE TO RELATED APPLICATION(S)

This application claims priority to U.S. Provisional Application Ser. No. 61/427,236 filed Dec. 27, 2010. The entire content of U.S. Provisional Application Ser. No. 61/427,236 is incorporated herein by reference.

BACKGROUND OF THE INVENTION

Pancreatitis is an inflammation of the pancreas. It has various causes. Once the gland becomes inflamed, the condition can progress to swelling of the gland and surrounding blood vessels, bleeding, infection, and damage to the gland. Digestive juices become trapped and start "digesting" the pancreas itself. If this damage persists, the gland may not be able to carry out normal functions.

Pancreatitis may be acute (new, short-term) or chronic (ongoing, long-term). Acute pancreatitis is a common disease that causes significant morbidity and mortality. Either type can be very severe, and lead to serious complications. Chronic pancreatitis begins as acute pancreatitis. If the pancreas becomes scarred during the attack of acute pancreatitis, it cannot return to its normal state. The damage to the gland continues, worsening over time.

Acute pancreatitis usually begins soon after the damage to the pancreas begins. Attacks are typically very mild. Mild attacks may last for a short time and usually resolves completely as the pancreas returns to its normal state. Some people have only one attack, whereas other people have more than one attack. About 20% of cases however, are very severe. There are reports that more than 300,000 patients are admitted per year for pancreatitis in the United States, and about 20,000 of those patients die from the disease. Pancreatitis can occur in people of all ages, although it is very rare in children. Pancreatitis occurs in men and women, although chronic pancreatitis is more common in men than in women.

Alcohol abuse and gallstones are the two main causes of pancreatitis, accounting for 80%-90% of all cases. Pancreatitis from alcohol use usually occurs in patients who have been long-term alcohol drinkers for at least five to seven years. Most cases of chronic pancreatitis are due to alcohol abuse. Pancreatitis is often already chronic by the first time the person seeks medical attention (usually for severe pain). Gallstones form from a buildup of material within the gallbladder. A gallstone can block the pancreatic duct, trapping digestive juices inside the pancreas. Pancreatitis due to gallstones tends to occur most often in women older than 50 years of age.

The remaining 10%-20% of cases of pancreatitis have various causes, including the following: medications, exposure to certain chemicals, injury (trauma), as might happen in a car accident or a bad fall leading to abdominal trauma, hereditary disease, surgery and certain medical procedures, infections such as mumps (not common), abnormalities of the pancreas or intestine, or high fat levels in the blood. In about 15% of cases of acute pancreatitis and 40% of cases of chronic pancreatitis, the cause is never known.

High levels of triglycerides are associated with acute pancreatitis and considerable morbidity and mortality. In September of 2002, the National Institute of Health published its third report of the Expert Panel on Detection Evaluation, and Treatment of High Blood Cholesterol in Adults (Adult Treatment Panel III, or ATPIII guidelines). Although the focus of this report is on LDL-cholesterol and HDL-cholesterol levels, it also provides guidance for treatment of patients having high triglyceride levels. The report adopted a classification for triglyceride levels: normal triglycerides: below 150 mg/dL, borderline-high triglycerides: between 150-199 mg/dL, high triglycerides: between 200-499 mg/dL, and very high triglycerides: ≥500 mg/dL. For all the groups the guidelines indicates that the primary aim of therapy is to reach the target goal for LDL cholesterol. For patients with borderline or high triglyceride level the guidelines recommend that treatment should focus on weight reduction, increased physical activity, treatment with LDL-lowering drugs, and if used with appropriate caution, nicotinic acid or fibrate can be added to achieve the non-HDL cholesterol goal by further lowering of VLDL cholesterol. The guidelines are clear that in those cases in which triglycerides are very high (≥500 mg/dL), that the initial aim of therapy is to prevent acute pancreatitis through triglyceride lowering. The guideline recommend that this approach requires very low fat diets, weight reduction, increased physical activity, and usually a triglyceride-lowering drug (fibrate or nicotinic acid).

Although fibrates are generally well-tolerated in most persons, they are associated with well-established side effects. All drugs in this class appear to increase the likelihood of cholesterol gallstones. In addition, because fibrates bind strongly to serum albumin, they may displace other drugs that bind with albumin. For example, fibrates displace warfarin from its albumin-binding sites, thereby increasing warfarin's anticoagulant effect. Fibrates are excreted primarily by the kidney; consequently, elevated serum levels occur in persons with renal failure and risk for myopathy is greatly increased. The fibrate gemfibrozil is a CYP3A4 substrate and as such inhibits the metabolism of some statins, including atorvastatin, lovastatin and simvastatin. This competition decreases rate of metabolism of the drugs resulting in their accumulation. This effect increases the risk for myopathy, which can lead to rhabdomyolysis. Fibrates also interfere with the metabolism of the protease inhibitors, indinavir, ritonavir, saquimavir and nelfinavir which are both substrates and inhibitors of CYP3A4. Gemcabene has been shown to have a low level of inhibition of CYP3A4, however in a drug-drug interaction study with simvastatin (a CYP3A4 substrate) showed no clinically relevant effect.

Dyslipidemia is common in persons with HIV infection on highly active antiretroviral therapy (HAART), the typical pattern includes elevated total cholesterol, LDL, and triglyceride, which may be markedly elevated. The hypertriglyceridemia appears to be related to the treatment with protease inhibitors. Treatment decisions in HIV treatment are complex and must include consideration of multiple potential drug-drug interactions in view of the selection of lipid-lowering drugs. Statins remain the most effective drugs for lowering LDL cholesterol however because fibrates and certain statins and protease inhibitors are CYP3A4 substrates, combination therapy can lead to increased levels of statin which are associated with an increased incidence of myopathy.

Nicotinic acid is also associated with side-effects. In persons with elevated serum glucose; nicotinic acid may worsen hyperglycemia and triglycerides may actually increase. Some patients treated with nicotinic acid develop severe liver toxicity.

There currently are no effective therapeutic treatments for the pancreatitis. Current treatments include giving antibiotics to treat or prevent infections, pain relievers, and changes in diet. Thus, in patients at risk for developing pancreatitis, e.g. with triglyceride levels ≥500 mg/dL. It is desirable to treat at risk patients prophylactically before pancreatitis occurs, or reoccurs, and also to treat patients with pancreatitis. Given the inadequacies of current treatment, there is a need for improved therapies for treating patients having high triglyceride levels.

SUMMARY OF THE INVENTION

The present disclosure provides methods for decreasing a subject's risk for developing pancreatitis comprising administering to a subject an effective amount of a carboxyalkylether of formula

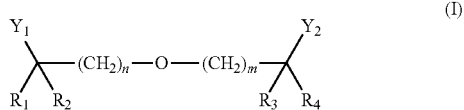

or a pharmaceutically acceptable salt or ester thereof, or a precursor (pro-drug) thereof that metabolizes in situ to the active carboxyalkylether acid or a salt thereof, wherein $Y_1$, $Y_2$, $R_1$, $R_2$, $R_3$, $R_4$, n, and m are as defined herein.

The present disclosure also provides methods for treating pancreatitis in a subject suffering from pancreatitis comprising administering to a mammal an effective amount of a carboxyalkylether of formula (I):

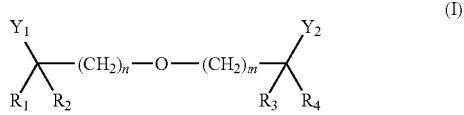

or a pharmaceutically acceptable salt or ester thereof, or a precursor (pro-drug) thereof that metabolizes in situ to the active carboxyalkylether acid or a salt thereof, wherein $Y_1$, $Y_2$, $R_1$, $R_2$, $R_3$, $R_4$, n, and m are as defined herein.

BRIEF DESCRIPTION OF THE DRAWING(S)

FIG. 1 is a graph showing the effect of treatment with gemcabene, 150 mg/day, on plasma triglycerides and HDL-C of a subject with an initial plasma triglyceride level of greater than 500 mg/dL.

FIGS. 2a-e are graphs showing the effect of treatment with placebo or gemcabene at dose levels of 150 mg, 300 mg, 600 mg and 900 mg per day on plasma triglyceride levels.

FIGS. 3a-e are graphs showing the effect of treatment with placebo, or gemcabene at dose levels of 150 mg, 300 mg, 600 mg and 900 mg per day on plasma HDL-C levels.

FIGS. 4a-e are graphs showing the effect of treatment with placebo, or gemcabene at dose levels of 150 mg, 300 mg, 600 mg and 900 mg per day on plasma ApoA-I levels.

FIGS. 5a-e are graphs showing the effect of treatment with placebo, or gemcabene at dose levels of 150 mg, 300 mg, 600 mg and 900 mg per day on plasma ApoC-III levels.

FIGS. 6a-e are graphs showing the effect of treatment with placebo, or gemcabene at dose levels of 150 mg, 300 mg, 600 mg and 900 mg per day on plasma VLDL-C levels.

FIGS. 7a-e are graphs showing the effect of treatment with placebo, or gemcabene at dose levels of 150 mg, 300 mg, 600 mg and 900 mg per day on plasma hsCRP levels.

FIGS. 8a-e are graphs showing the effect of treatment with placebo, or gemcabene at dose levels of 150 mg, 300 mg, 600 mg and 900 mg per day on plasma ApoB levels.

DETAILED DESCRIPTION OF THE INVENTION

As used herein, the term "carboxyalkylether" includes the free acid, pharmaceutically acceptable salts and esters thereof, and prodrugs thereof that are converted to the free acid, or salt or hydrate thereof. Such compounds are known in the art, as well as their synthesis and formulation.

"Subject" or "Patient" are used interchangeably.

The term "treating" or other forms of the word such as "treatment", or "treat" is used herein to mean that administration of a compound of the present invention mitigates a disease or a disorder in a host and/or reduces, inhibits, or eliminates a particular characteristic or event associated with a disorder (e.g., reduced steroidogenesis). Thus, the term "treatment" includes, preventing a disorder from occurring in a host, particularly when the host is predisposed to acquiring the disorder; inhibiting the disorder; and/or alleviating or reversing the disorder. Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state be completely avoided.

"HDL-C" is an abbreviation for high density lipoprotein cholesterol.

"LDL-C" is an abbreviation for low density lipoprotein cholesterol.

"VLDL-C" is an abbreviation for very low density lipoprotein cholesterol.

"apo A-I" is an abbreviation for apolipoprotein A-I.
"Apo A-II" is an abbreviation for apolipoprotein A-II.
"Apo A-V" is an abbreviation for apolipoprotein A-V.
"Apo B" is an abbreviation for apolipoprotein B.
"Apo C-I" is an abbreviation for apolipoprotein C-I.
"Apo C-II" is an abbreviation for apolipoprotein C-II.
"Apo C-III" is an abbreviation for apolipoprotein C-III.
"Apo E" is an abbreviation for apolipoprotein E.
"hs CRP" is an abbreviation for high sensitivity C-reactive protein.

Throughout the description and claims of this specification the word "comprise" and other forms of the word, such as "comprising" and "comprises," means including but not limited to, and is not intended to exclude, for example, other additives, components, integers, or steps.

As used herein, the singular forms "a", "an", and "the" include plural references unless the context clearly dictates otherwise "Between" as used herein is inclusive, e.g., "between 1 mg and 5000 mg" includes 1 mg and 5000 mg.

"About" when used in conjunction with a number includes the number itself, for example, "from about 1 mg to about 5000 mg" includes the range "from 1 mg to 5000 mg".

"From" as used herein is inclusive, e.g., "from 1 mg to 5000 mg" includes 1 mg and 5000 mg.

As used herein, "alkyl" refers to a saturated aliphatic hydrocarbon containing 1-6 carbon atoms. An alkyl can be straight or branched.

As used herein, "alkenyl" refers to an aliphatic carbon that contains 2-6 carbon atoms and at least one double bond. Like an alkyl, an alkenyl can be straight or branched.

As used herein, "alkynyl" refers to an aliphatic carbon that contains 2-6 carbon atoms and at least one triple bond. Like an alkyl, an alkynyl can be straight or branched.

The term "carbocyclic ring" encompasses cycloalkyl and cycloalkenyl rings. Carbocyclic rings can be optionally substituted with one or more substituents such as aliphatic (e.g., alkyl, alkenyl, or alkynyl).

As used herein, an "effective dose" is that amount of the compound, or pharmaceutically acceptable composition thereof, which is effective to treat or prevent pancreatitis.

One embodiment of the invention is a method of decreasing a subject's risk for developing pancreatitis comprising administering to a subject in need thereof, an effective dose of a compound of formula (I):

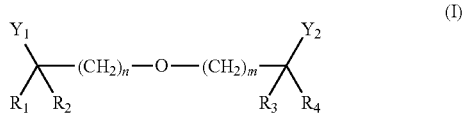

wherein n, and m independently are integers from 2 to 9; each occurrence of $R_1$, $R_2$, $R_3$, and $R_4$ is independently $C_1$-$C_6$ alkyl, $C_2$-$C_6$ alkenyl, $C_2$-$C_6$ alkynyl, or $R_1$ and $R_2$ taken together with the carbon to which they are attached form a carbocyclic ring having from 3 to 6 carbons, or $R_3$ and $R_4$ together with the carbon to which they are attached, form a carbocyclic ring having from 3 to 6 carbons; $Y_1$ and $Y_2$ independently are —COOH, —CHO, tetrazole, and —COOR$_5$; $R_5$ is $C_1$-$C_6$ alkyl, $C_2$-$C_6$ alkenyl, $C_2$-$C_6$ alkynyl; or an ester or a salt thereof, or a precursor thereof that metabolizes in vivo to the compound of formula (I) or the free acid, a salt, or a hydrate thereof.

Another embodiment is a method of treating pancreatitis in a subject suffering from pancreatitis comprising administering to a subject in need thereof, an effective dose of a compound of formula (I):

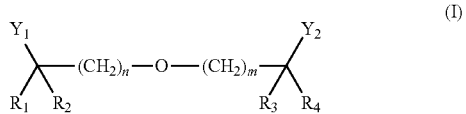

wherein n, and m independently are integers from 2 to 9; each occurrence of $R_1$, $R_2$, $R_3$, and $R_4$ is independently $C_1$-$C_6$ alkyl, $C_2$-$C_6$ alkenyl, $C_2$-$C_6$ alkynyl, or $R_1$ and $R_2$ taken together with the carbon to which they are attached form a carbocyclic ring having from 3 to 6 carbons, or $R_3$ and $R_4$ together with the carbon to which they are attached, form a carbocyclic ring having from 3 to 6 carbons; $Y_1$ and $Y_2$ independently are —COOH, —CHO, tetrazole, and —COOR$_5$; $R_5$ is $C_1$-$C_6$ alkyl, $C_2$-$C_6$ alkenyl, $C_2$-$C_6$ alkynyl; or an ester or a salt thereof, or a precursor thereof that metabolizes in vivo to the compound of formula (I) or the free acid, a salt, or a hydrate thereof.

In some embodiments the compound of formula (I) is administered as a free acid. In other embodiments the compound administered is a pharmaceutically acceptable salt of a compound of formula (I). In yet other embodiments the compound administered is an ester of a compound of formula (I). In some embodiments the compound administered is a precursor (pro-drug) of formula (I) that metabolizes in vivo to the active carboxyalkylether acid or a salt of formula (I).

In some embodiments, n is 2, or n is 3, or n is 4, or n is 5, or n is 6, or n is 7, or n is 8, or n is 9. In some embodiments, m is 2, or n is 3, or m is 4, or m is 5, or m is 6, or m is 7, or m is 8, or m is 9. In some embodiments, n and m are both 2, or n and m are both 3, or n and m are both 4, or n and m are both 5, or n and m are both 6, or n and m are both 7, or n and m are both 8, or n and m are both 9.

In some embodiments $R_1$, $R_2$, $R_3$, and $R_4$ independently are $C_1$-$C_6$ alkyl. In some embodiments $R_1$, $R_2$, $R_3$, and $R_4$ are all $C_1$-$C_6$ alkyl. In some embodiments $R_1$, $R_2$, $R_3$, and $R_4$ independently are $C_2$-$C_6$ alkenyl. In some embodiments $R_1$, $R_2$, $R_3$, and $R_4$ independently are $C_2$-$C_6$ alkynyl. In some embodiments $R_1$, $R_2$, $R_3$, and $R_4$ are —$CH_3$. In some embodiments $R_1$, $R_2$, $R_3$, and $R_4$ are —$CH_2CH_3$. In some embodiments $R_1$, $R_2$, $R_3$, and $R_4$ are —$CH_2CH_2CH_3$. In some embodiments $R_1$, $R_2$, $R_3$, and $R_4$ are all $C_2$-$C_6$ alkenyl. In some embodiments $R_1$, $R_2$, $R_3$, and R4 are all $C_2$-$C_6$ alkynyl. In some embodiments $R_1$ and $R_2$ taken together with the carbon to which they are attached form a carbocyclic ring having from 3 to 6 carbons. In other embodiments $R_3$ and $R_4$ together with the carbon to which they are attached, form a carbocyclic ring having from 3 to 6 carbons.

In some embodiments $Y_1$ and $Y_2$ are both —COOH. In some embodiments $Y_1$ and $Y_2$ are both —CHO. In some embodiments $Y_1$ and $Y_2$ are both -tetrazole. In some embodiments $Y_1$ and $Y_2$ are both $CH_2(OH)$. In some embodiments $Y_1$ and $Y_2$ are both —COOR$_5$ and $R_5$ is $C_1$-$C_6$ alkyl. In some embodiments $Y_1$ and $Y_2$ are both —COOR$_5$ and $R_5$ is $C_2$-$C_6$ alkenyl. In some embodiments $Y_1$ and $Y_2$ are both —COOR$_5$ and $R_5$ is $C_2$-$C_6$ alkynyl.

In another embodiment, the compound is a compound formula I, wherein n an m are the same integer, and $R_1$, $R_2$, $R_3$, and $R_4$ independently are $C_1$-$C_6$ alkyl. In yet another embodiment, the compound is a compound of formula I, wherein $Y_1$ and $Y_2$ are the same and are —COOH or —COOR$_5$, and $R_5$ is $C_1$-$C_6$ alkyl. In a preferred embodiment, the compound is a compound formula I, wherein $Y_1$ and $Y_2$ are COOH, $R_1$, $R_2$, $R_3$, and $R_4$ are methyl, and n and m are the same and are an integer selected from 2, 3, 4, or 5, preferably n and m are the same and are 4 or 5. Most preferably n and m are 4. In still another embodiment, the compound is a compound of formula I, wherein $Y_1$ and $Y_2$ are —COOH, and $R_1$, $R_2$, $R_3$, and $R_4$ independently are $C_1$-$C_6$ alkyl, and n and m are 4. In another embodiment the compound is a compound of formula I, wherein $Y_1$ and $Y_2$ are —COOH, n and m are 4, $R_1$, $R_2$, $R_3$, and $R_4$ are methyl. In another embodiment the compound is a compound of formula I, wherein $Y_1$ and $Y_2$ are —COOH, n and m are 5, $R_1$, $R_2$, $R_3$, and R4 are methyl. In yet another embodiment, the compound is a compound of formula I, wherein $Y_1$ and $Y_2$ are —$CH_2OH$, and n and m are 4. In another embodiment, the compound is a compound of formula I, wherein $Y_1$ and $Y_2$ are —$CH_2OH$, n and m are 4 and $R_1$, $R_2$, $R_3$, and $R_4$ are methyl.

Another embodiment of the invention is a method of decreasing a subject's risk for developing pancreatitis comprising administering to a subject in need thereof, an effective dose of a compound of formula (I), wherein n and m are each 4; each occurrence of $R_1$, $R_2$, $R_3$, and $R_4$ is independently $C_1$-$C_6$ alkyl, $C_2$-$C_6$ alkenyl, $C_2$-$C_6$ alkynyl, or $R_1$ and $R_2$ taken together with the carbon to which they are attached form a carbocyclic ring having from 3 to 6 carbons, or $R_3$ and $R_4$ together with the carbon to which they are attached, form a carbocyclic ring having from 3 to 6 carbons; $Y_1$ and $Y_2$ independently are —COOH, —CHO, tetrazole, and —COOR$_5$; $R_5$ is $C_1$-$C_6$ alkyl, $C_2$-$C_6$ alkenyl, $C_2$-$C_6$ alkynyl; or an ester or pharmaceutically acceptable salt thereof.

Another embodiment of the invention is a method of decreasing a subject's risk for developing pancreatitis comprising administering to a subject in need thereof, an effective dose of a compound of formula (I), wherein n and m are the same and are 3, 4, or 5; each occurrence of $R_1$, $R_2$, $R_3$, and $R_4$ is independently $C_1$-$C_6$ alkyl; $Y_1$ and $Y_2$ are the same and are —COOH, —CHO, or tetrazole; or an ester or pharmaceutically acceptable salt thereof.

Another embodiment of the invention is a method of decreasing a subject's risk for developing pancreatitis comprising administering to a subject in need thereof, an effective dose of a compound of formula (I), wherein n and m are the same and are 3, 4, or 5; $R_1$ and $R_2$ are the same and are $C_1$-$C_6$ alkyl; $R_3$, and $R_4$ are the same and are $C_1$-$C_6$ alkyl; $Y_1$ and $Y_2$ are the same and are —COOH, —CHO, or tetrazole; or an ester or pharmaceutically acceptable salt thereof.

Another embodiment of the invention is a method of decreasing a subject's risk for developing pancreatitis comprising administering to a subject in need thereof, an effective dose of a compound of formula (I), wherein n and m and are each 4; $R_1$ and $R_2$ are the same and are $C_1$-$C_6$ alkyl; R3, and $R_4$ are the same and are $C_1$-$C_6$ alkyl; $Y_1$ and $Y_2$ are the same and are —COOH; or pharmaceutically acceptable salt thereof.

Another embodiment is a method of treating pancreatitis in a subject suffering from pancreatitis comprising administering to a subject in need thereof, an effective dose of a compound of formula (I), wherein n and m are each 4; each occurrence of $R_1$, $R_2$, $R_3$, and $R_4$ is independently $C_1$-$C_6$ alkyl, $C_2$-$C_6$ alkenyl, $C_2$-$C_6$ alkynyl, or $R_1$ and $R_2$ taken together with the carbon to which they are attached form a carbocyclic ring having from 3 to 6 carbons, or $R_3$ and $R_4$ together with the carbon to which they are attached, form a carbocyclic ring having from 3 to 6 carbons; $Y_1$ and $Y_2$ independently are —COOH, —CHO, tetrazole, and —COOR$_5$; $R_5$ is $C_1$-$C_6$ alkyl, $C_2$-$C_6$ alkenyl, $C_2$-$C_6$ alkynyl; or an ester or pharmaceutically acceptable salt thereof.

Another embodiment is a method of treating pancreatitis in a subject suffering from pancreatitis comprising administering to a subject in need thereof, an effective dose of a compound of formula (I), wherein n and m are the same and are 3, 4, or 5; each occurrence of $R_1$, $R_2$, $R_3$, and $R_4$ is independently $C_1$-$C_6$ alkyl; $Y_1$ and $Y_2$ are the same and are —COOH, —CHO, or tetrazole; or an ester or pharmaceutically acceptable salt thereof.

Another embodiment is a method of treating pancreatitis in a subject suffering from pancreatitis comprising administering to a subject in need thereof, an effective dose of a compound of formula (I), wherein n and m are the same and are 3, 4, or 5; $R_1$ and $R_2$ are the same and are $C_1$-$C_6$ alkyl; $R_3$, and $R_4$ are the same and are $C_1$-$C_6$ alkyl; $Y_1$ and $Y_2$ are the same and are —COOH, —CHO, or tetrazole; or an ester or pharmaceutically acceptable salt thereof.

Another embodiment is a method of treating pancreatitis in a subject suffering from pancreatitis comprising administering to a subject in need thereof, an effective dose of a compound of formula (I), wherein n and m and are each 4; $R_1$ and $R_2$ are the same and are $C_1$-$C_6$ alkyl; R3, and $R_4$ are the same and are $C_1$-$C_6$ alkyl; $Y_1$ and $Y_2$ are the same and are —COOH; or pharmaceutically acceptable salt thereof.

Compounds of formula (I) can be referred to generally as carboxyalkylethers. Carboxyalkylethers are a class of compounds described by Bisgaier et al. in U.S. Pat. No. 5,648, 387, and by Ando et al. in U.S. Pat. No. 6,861,555, both patents are incorporated herein by reference. These compounds are described as having a number of biological activities, including raising levels of high density lipoproteins (HDL), and are said to be useful for treating cardiovascular disorders, diabetes, and other medical conditions, neither patent describes the use of gemcabene to treat pancreatitis. The compounds can be used alone or in combination with other agents such as statins, for example as described by Bisgaier et al. in U.S. Patent Publication No. 2002/0103252, which is incorporated herein by reference.

In one embodiment of this invention, the carboxyalkylether of formula (I), is a compound known as "CI-1027", as "gemcabene", and as "PD 72953" (Bays et. al. Am. J. Cardiol. 2003; 92:538-543, incorporated herein by reference). The chemical name of this compound is 6,6'-oxybis-(2,2'-dimethylhexanoic acid) or alternately 6-(5-carboxy-5-methyl-hexyloxy)-2,2-dimethylhexanoic acid.

In another embodiment gemcabene is administered as a pharmaceutical salt. In yet another embodiment, gemcabene is administered as a calcium salt.

In another embodiment gemcabene is administered as the anhydrous monocalcium salt. The structure of the anhydrous monocalcium salt of gemcabene is:

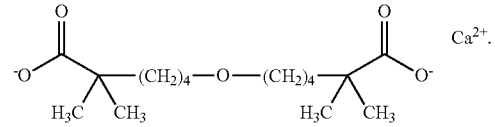

In an embodiment gemcabene is administered as a hydrate. In another embodiment gemcabene is administered as the hydrate of the monocalcium salt, as described in U.S. Pat. No. 6,861,555. The structure of the hydrate of the monocalcium salt of gemcabene is:

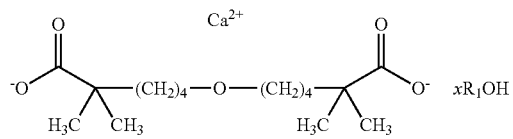

In another embodiment, gemcabene is administered in a crystalline form.

Several compounds are known that are precursors or pro-drugs of the carboxyalkylethers of the present disclosure, namely compounds that when administered to a subject are metabolized or otherwise converted in vivo to the carboxyalkylether as the free acid, salt, or hydrate thereof. See Goel, U.S. Pat. No. 7,345,190 "Carnitine conjugates as dual pro-drugs and uses thereof", incorporated herein by reference. Other compounds that are metabolized in situ include those described in U.S. Pat. Nos. 6,410,802; 6,459,003; 6,645,170; 6,713,507; 6,790,953, and 7,192,940, all of which are incorporated herein by reference.

Thus, another embodiment is a method of decreasing a subject's risk for developing pancreatitis comprising administering to a subject in need thereof, an effective dose of a pro-drug of a compound of formula (I). In a particular embodiment, the method of decreasing a subject's risk for developing pancreatitis comprises administering to a subject in need thereof, an effective dose of a pro-drug of gemcabene.

The effective daily dose is typically from about 0.1 mg/kg to about 100 mg/kg. The daily dose typically utilized for administration to a human subject is between about 25 and about 1200 mg, or between about 50 and about 1000 mg, or between about 50 and about 900 mg, or between about 100 and about 900 mg, or between about 100 and about 600 mg, or between about 150 and about 600 mg, or about 150 mg, or about 300 mg, or about 600 mg, or about 900 mg, or between 10 and 1500 mg, or between 25 and 1200 mg, or between 50 and 1000 mg, or between 50 and 900 mg, or between 100 and 900, or between 100 and 600 mg, or between 150 and 600 mg, or 150 mg, or 300 mg, or 600 mg, or 900 mg. The daily dose can be by non-limiting example, 25 mg, or 30 mg, or 35 mg, or 40 mg, or 45 mg, or 50 mg, or 55 mg, or 60 mg, or 65 mg, or 70 mg, or 75 mg, or 80 mg, or 85 mg, or 90 mg, or 95 mg, or 100 mg, 125 mg, or 150 mg, or 175 mg, or 200 mg, or 225 mg, or 250 mg, or 275 mg, or or 300 mg, or 325 mg, or 350 mg, or 375 mg, or 400 mg, or 425 mg, or 450 mg, or 475 mg, or 500 mg, or 525 mg, or 550 mg, or 575 mg, or 600 mg, or 625 mg, or 650 mg, or 675 mg, or 700 mg, or 725 mg, or 750 mg, or 775 mg, or 800 mg, or 825 mg, or 850 mg, or 875 mg, or 900 mg, or 925 mg, or 975 mg, or 1000 mg, or 1025 mg, or 1050 mg, or 1075 mg, or 1100 mg, or 1125 mg, or 1150 mg, or or 1175 mg, or 1200 mg.

For gemcabene the preferred daily dose is 150 mg, or 300 mg, or 600 mg. Most preferably the daily dose of gemcabene is 150 mg or 300 mg.

The compounds of the present disclosure may be administered 1, 2, 3, 4 or 5 times per day. Preferably the compounds are administered 1 or 2 times a day. More preferably the compounds are administered 1 time per day.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of the compound administered will also depend upon the particular compound in the composition.

While the causes of pancreatitis include diet and excess alcohol consumption, many subjects suffering from pancreatitis or at risk of developing pancreatitis who have normal diets and are not alcoholic nevertheless have severely elevated levels of blood triglycerides, for example levels of 1000 mg/dl or more. The cause of highly elevated circulating triglycerides is also genetic in origin. It is well known subjects with genetic variations in the enzyme lipoprotein lipase can have a less than normal ability to catabolize circulating triglyceride-rich lipoproteins and leads to elevated circulating triglycerides. It is also known that elevated plasma apo C-I, apo C-II, and apo C-III levels inhibits the clearance of triglyceride-rich lipoproteins, while elevated levels of apo E can facilitate clearance of triglyceride-rich lipoproteins. It is also known that apo C-II is an activator of lipoprotein lipase and its deficiency, a rare genetic condition, leads to highly elevated triglycerides. Apo A-V is also an activator of lipoprotein lipase and a variant form of apo A-V, the apo A-V S19W polymorphism, is associated with markedly elevated triglycerides. Thus, elevated circulating triglycerides may originate due to genetic factors, environmental factors or a combination of genetic and environmental factors. Another aspect of this invention is a method for treating or preventing pancreatitis in subjects having blood triglyceride levels of 1000 mg/dl or more comprising administering to such subject an effective dose of gemcabene.

Compounds useful in the present invention can be formulated as pharmaceutical compositions and administered to a subject, such as a human subject in a variety of forms adapted to the chosen route of administration, i.e., orally, transdermal, and parenterally, by intravenous, intramuscular or subcutaneous routes. Such compositions and methods for their preparation are well known and may be found, for example, in Remington's Pharmaceutical Sciences, 19th Edition (Mack Publishing Company, 1995). For example, typical formulations for gemcabene are described in U.S. Pat. No. 5,648,387. In one embodiment, gemcabene is formulated with common excipients and carriers such as starch, binders, diluents and the like, and molded into tablets, or encapsulated into gelatin capsules, all for convenient oral administration. Gemcabene has excellent physical properties that enable formulation as syrups, elixirs, slow release lozenges, and other common oral formulation types. Gemcabene can additionally be formulated with saline and other common excipients for administration by the intravenous route, intraperitoneal, and similar parenteral routes. Transdermal patches can be made with binders and common adjuvants, and rectal formulations using pharmaceutically acceptable waxes can be made utilizing common formulation technologies that are well known to those skilled in the art of pharmaceutical formulations.

Compounds of the present invention may be administered alone or in combination with an additional agent. Such therapies include, but are not limited to simultaneous or sequential administration of the compound of the present invention and the additional agent. For example the compounds of the invention can be administered with drugs including, but not limited to, cholesterol lowering drugs including, but not limited to, statins such as, atorvastatin, lovastatin, simvastatin, pravastatin rosuvastatin, fluvastatin, pitastatin; protease inhibitors such as, amprenavir, tipranavir, indinavir, saquinavir, lopinavir, ritonavir, fosamprenavir, ritonavir, darunavir, nelfinavir, brecanavir, atazanavir sulfate; cholesterol absorption inhibitors such as Zetia; bile acid sequestrants such as cholestryamine; and apoB synthesis inhibitors, such as ISIS 301012 (an apoB antisense). The methods of the present invention also include embodiments in which a compound of formula (I) is administered in conjunction with a procedural for reducing LDL e.g., apoB plasmapheresis.

EXAMPLES

The following examples are illustrative only and are not to be construed as limiting the invention in any respect.

Example 1

A randomized, double-blind, placebo-controlled study was conducted to evaluate the efficacy and tolerability of gemcabene in patients with HDL cholesterol levels <35 mg/dL. Patients were stratified based on whether mean serum triglyceride (TG) levels were <200 mg/dL or ≥200 mg/dL. Within each TG stratum, patients were randomized to receive either 150, 300, 600 or 900 mg of gemcabene, or placebo, once daily for 12 weeks.

Patients were evaluated for percent change from baseline levels of serum HDL cholesterol, serum LDL cholesterol, TG, apolipoproteins A-I, A-II, B, C-III, and E, hs CRP and non-HDL cholesterol levels. Blood samples were measured at screening, randomization and at −8, −4, −2 weeks, baseline, and 2, 4, and 12 weeks after the start of study medication. In addition, HDL-C, LDL-C and TG levels were measured at 2 and 4 weeks before starting study medication. Bays H. E. et al. Am J Cardiol (2003) vol. 92, pp 538-543, describes one view of this study but did not disclose data or discuss the effect of gemcabene on the specific subset of patients having TG levels greater than 500 mg/dL.

When the data were examined for the subset of patients entering the study having TG levels greater than 500 mg/dL, an unexpectedly large decrease in TG levels for those patients treated with gemcabene was seen as compared with the broader group of patients having triglyceride levels ≥200 mg/dL. Twenty-seven patients having TG levels >500 mg/dL were evaluated in the study.

FIG. 1 is a graph showing the change in the serum TG and HDL-C levels for one of these patients at time points of about 8, 4, and 2 weeks prior to treatment, baseline, and 2, 4, 8, and 12 weeks post-treatment with gemcabene at 150 mg/day. At the initiation of treatment, the patient's TG level was 550 mg/dL. The data show that the patient's triglyceride level fell dramatically over this period to 210 mg/dL (by 62%) and HDL-C levels increased by 27%.

FIGS. 2a-e, 3a-e, 4a-e, 5a-e, 6a-e, 7a-e and 8a-e are graphs illustrating the serum levels of TG, HDL-C, ApoA-I, ApoC-III, VLDL-C, hs CRP, and ApoB for individual patients at baseline and at 12 weeks post treatment with doses of 150, 300, 600, and 900 mg/day of gemcabene, or placebo.

Tables 1-7 provide the data expressed as average percent and mean percent decrease or increase, as appropriate, for each of these parameters at each of the doses tested.

As demonstrated by the data, in these patients having TG levels >500 mg/dL, gemcabene is most effective at reducing triglyceride levels at the 150 and 300 mg doses, showing an average decrease in TG of 52% and 61% respectively. The 150 and 300 mg doses are also most effective at increasing HDL-C, decreasing ApoC-III, and VLDL-C. The magnitude of the change in triglyceride levels at these doses is greater than would have been expected based on the data reported in Bays et al., which showed a reduction in triglyceride levels of 26.6% and 38.9% for the 150 and 300 mg doses, respectively.

TABLE 1

Triglycerides mg/dL

| Gemcabene Dose/Day | n | Average % decrease |
|---|---|---|
| 0 | 5 | 30.50 |
| 150 | 6 | 52.09 |
| 300 | 6 | 61.18 |
| 600 | 4 | 36.44 |
| 900 | 6 | 0.90 |

TABLE 2

HDL-C mg/dL

| Gemcabene Dose/Day | n | Average % increase |
|---|---|---|
| 0 | 5 | −2.27 |
| 150 | 6 | 32.59 |
| 300 | 6 | 11.69 |
| 600 | 4 | −4.02 |
| 900 | 6 | 1.03 |

TABLE 3

ApoA-I mg/dL

| Gemcabene Dose/Day | n | Average % increase |
|---|---|---|
| 0 | 5 | −9.25 |
| 150 | 5 | 9.27 |
| 300 | 6 | −6.17 |
| 600 | 4 | −3.31 |
| 900 | 6 | 0.47 |

TABLE 4

ApoC-III mg/dL

| Gemcabene Dose/Day | n | Average % decrease |
|---|---|---|
| 0 | 5 | 34.70 |
| 150 | 5 | 36.95 |
| 300 | 6 | 49.41 |
| 600 | 4 | 30.89 |
| 900 | 6 | 20.36 |

TABLE 5

VLDL-C mg/dL

| Gemcabene Dose/Day | n | Average % decrease |
|---|---|---|
| 0 | 5 | 36.65 |
| 150 | 5 | 48.50 |
| 300 | 6 | 51.86 |
| 600 | 3 | 28.73 |
| 900 | 6 | 17.10 |

TABLE 6 hs-CRP mg/L

| Gemcabene Dose/Day | n | Average % decrease |
|---|---|---|
| 0 | 5 | −171.00 |
| 150 | 5 | −4.02 |
| 300 | 6 | −429.19 |
| 600 | 4 | 33.50 |
| 900 | 6 | 66.64 |

TABLE 7

ApoB mg/dL

| Gemcabene Dose/Day | n | Average % decrease |
|---|---|---|
| 0 | 5 | 0.29 |
| 150 | 5 | −16.15 |
| 300 | 6 | 1.25 |
| 600 | 4 | −3.70 |
| 900 | 6 | 2.26 |

Example 2

Oral Formulation

| Ingredient | Amount |
|---|---|
| Gemcabene | 400 mg |
| Corn starch | 150 mg |
| Methyl cellulose | 50 mg |
| Dextrose | 50 mg |
| Total | 650 mg |

The above ingredients are blended to uniformity and molded into a tablet that is administered to a subject to treat or prevent pancreatitis.

Example 3

| Ingredient | Amount |
| --- | --- |
| 6,6'-oxybis-(2,2'-dimethylhexanoic acid monocalcium salt (API) | 1800 g |
| Lactose | 750 g |
| Corn Starch | 300 g |
| Gelatin | 120 g |
| Water | 1000 g |
| Magnesium Sterate | 30 |

The API, lactose, and 150 g of the corn starch are blended with a solution of the gelatin in the water. The wet granulation is screened, dried, and rescreened. The dried granules are blended with the magnesium stearate and the remaining corn starch, and the mixture is compressed into 500 mg tablets. Each tablet contains 300 mg of the API.

Example 4

| Ingredient | Amount |
| --- | --- |
| 6,6'-oxybis-(2,2-dimethylhexanoic acid) | 3.0 g |
| Polyoxyethylene sorbitan monosterate | 0.1 cc |
| Sodium carboxymethyl cellulose | 0.3 g |
| Complex Magnesium Aluminum Silicate | 0.5 g |
| Sugar | 10 g |
| Glycerin | 2 cc |
| Sodium benzoate | 0.5 g |
| Sodium citrate | 0.2 g |
| Approved red dye | 1 mg |
| Cherry flavor | 0.02 cc |
| Distilled water qs | 100 cc |

The polyoxyethylene sorbitan monostearate can be a product such as polysorbate 60 or Tween 60. The complex magnesium-aluminum silicate is a gel-forming agent. A product such as Veegum H. V. can be used. This substance is hydrated overnight in 10 cc distilled water. A mixture is prepared from the polyoxyethylene sorbitan monostearate, imitation cherry flavor, 30 cc of distilled water, and the dialkyl ether and passed through a homogenizer. With vigorous stirring, the sugar, glycerin, sodium citrate, sodium benzoate, and sodium carboxymethyl cellulose are added, followed by hydrated complex magnesium-aluminum silicate and a solution of the red dye in 2 cc of water. The resulting suspension is homogenized, adjusted to pH 5.0 with citric acid, and diluted to a final volume of 100 cc with distilled water. A 55-cc oral dosage unit of this suspension contains 150 mg of the dialkyl ether. If desired, the red dye and imitation cherry flavor can be omitted or replaced by other coloring and flavoring agents.

Example 5

A male patient 66 years of age, as part of a routine annual examination, has blood tests which reveal that the patient has an LDL-C level of 200 mg/dl and a triglyceride level of 1030 mg/dl. This high triglyceride level places him at high risk for developing pancreatitis. According to the ATPIII guidelines, the patient's treatment is initially targeted to address the high triglyceride level. The patient is administered gemcabene at a dose of 300 mg once per day and is placed on a low fat diet. At a 12-week follow-up appointment, the patient's triglyceride level is measured as 363 mg/dl, indicating that his risk of developing pancreatitis is significantly reduced.

What is claimed is:

1. A method of decreasing a subject's risk for developing pancreatitis comprising administering to a subject in need thereof, an effective dose of a compound

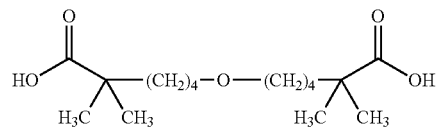

or a salt thereof, wherein the subject is a human and has a blood triglyceride level of 500 mg/dl or higher.

2. The method according to claim 1, wherein the subject has a LDL-cholesterol level greater than 100 mg/dL.

3. The method according to claim 1, wherein the amount of the compound administered is between about 100 mg/day and about 900 mg/day.

4. The method according to claim 1, wherein the amount of the compound administered is 150 mg/day, 300 mg/day, or 600 mg/day.

5. The method according to claim 1, wherein the amount of the compound administered is 150 or 300 mg/day.

6. The method according to claim 3, wherein the compound is administered once daily.

7. The method according to claim 1, wherein the compound is administered in combination with an agent selected from: a cholesterol lowering agent, a cholesterol absorption inhibitor, a bile acid sequestrant, an ApoB synthesis inhibitor, or a protease inhibitor.

8. The method according to claim 7, wherein the agent is a statin.

9. The method according to claim 1, wherein the compound is the nionocalcium salt

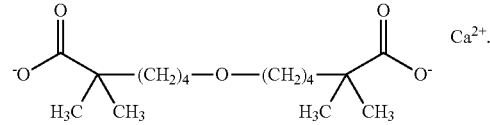

10. The method according to claim 9, wherein the subject has LDL-cholesterol level greater than 100 mg/dL.

11. The method according to claim 10, wherein the amount of the compound administered is between about 100 mg/day and about 900 mg/day.

12. The method according to claim 9, wherein the amount of the compound administered is 150 mg/day, 300 mg/day, or 600 mg/day.

13. The method according to claim 9, wherein the amount of the compound administered is 150 or 300 mg/day.

14. The method according to claim 11, wherein the compound is administered once daily.

15. The method according to claim 9, wherein the compound is administered in combination with an agent selected from: a cholesterol lowering agent, a cholesterol absorption inhibitor, a bile acid sequestrant, an ApoB synthesis inhibitor, or a protease inhibitor.

16. The method according to claim 15, wherein the agent is a statin.

* * * * *

UNITED STATES PATENT AND TRADEMARK OFFICE
CERTIFICATE OF CORRECTION

PATENT NO.        : 8,846,761 B2
APPLICATION NO.   : 13/334384
DATED             : September 30, 2014
INVENTOR(S)       : Charles L. Bisgaier It is certified that error appears in the above-identified patent and that said Letters Patent is hereby corrected as shown below:

In the Claims

Column 14, lines 41-50 should read

9. The method according to claim 1, wherein the compound is the monocalcium salt

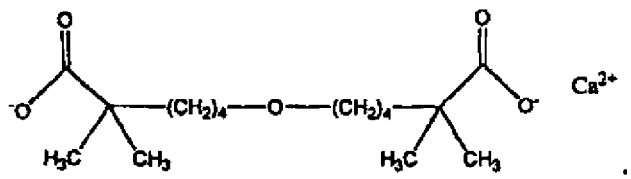

Signed and Sealed this
Twenty-fourth Day of March, 2015

Michelle K. Lee
*Director of the United States Patent and Trademark Office*